United States Patent
Song

(10) Patent No.: US 11,744,794 B2
(45) Date of Patent: Sep. 5, 2023

(54) INDIGO DARKENER AND HAIR DYEING PROCESS

(71) Applicant: Zikui Song, Jilin (CN)

(72) Inventor: Zikui Song, Jilin (CN)

( * ) Notice: Subject to any disclaimer, the term of this patent is extended or adjusted under 35 U.S.C. 154(b) by 77 days.

(21) Appl. No.: 17/619,448

(22) PCT Filed: Mar. 5, 2020

(86) PCT No.: PCT/CN2020/077895
§ 371 (c)(1),
(2) Date: Dec. 15, 2021

(87) PCT Pub. No.: WO2020/177730
PCT Pub. Date: Sep. 10, 2020

(65) Prior Publication Data
US 2022/0401351 A1    Dec. 22, 2022

(30) Foreign Application Priority Data

Mar. 7, 2019 (CN) .......................... 201910171616.8

(51) Int. Cl.
*A61Q 5/10* (2006.01)
*A61K 8/9789* (2017.01)

(52) U.S. Cl.
CPC .............. *A61K 8/9789* (2017.08); *A61Q 5/10* (2013.01); *A61K 2800/4324* (2013.01)

(58) Field of Classification Search
CPC .......... A61K 8/9789; A61K 2800/4324; A61K 8/23; A61K 8/987; A61K 8/492; A61K 8/9794; A61Q 5/10
USPC .......................................................... 8/407
See application file for complete search history.

(56) References Cited

U.S. PATENT DOCUMENTS

| | | | | |
|---|---|---|---|---|
| 2007/0067926 A1* | 3/2007 | Schmitt | ..................... | A61Q 5/10 8/405 |
| 2012/0210522 A1* | 8/2012 | Lim | ......................... | A61Q 5/10 8/409 |
| 2013/0081647 A1* | 4/2013 | Vohra | ....................... | A61Q 5/10 8/407 |
| 2014/0013520 A1* | 1/2014 | Lewis | ................. | C09B 29/0003 8/407 |
| 2015/0053226 A1* | 2/2015 | Bonauer | ................ | A61K 8/411 132/202 |

FOREIGN PATENT DOCUMENTS

| | | | | |
|---|---|---|---|---|
| CN | 1761448 A | * | 4/2006 | ............. A61Q 5/065 |
| CN | 105992583 A | | 10/2016 | |
| CN | 107223124 A | * | 9/2017 | ............... A61Q 5/10 |
| CN | 109674732 A | | 4/2019 | |
| FR | 2978042 A1 | | 1/2013 | |
| FR | 3004944 A1 | | 10/2014 | |
| JP | 3884818 B2 | * | 2/2007 | ............... A61Q 5/10 |
| KR | 20050026759 A | * | 3/2005 | ............... A61Q 5/10 |
| KR | 20060042467 A | | 5/2006 | |
| WO | 2019122436 A1 | | 6/2019 | |

OTHER PUBLICATIONS

International Search Report, China National Intellectual Property Administration, Application No. PCT/CN2020/077895 dated May 28, 2020, 4 pages, English Translation Attached, 3 pages.
The State Intellectual Property Office of People's Republic of China, First Search, Application No. 201910176168, 2 pages.
The State Intellectual Property Office of People's Republic of China, Supplementary Search, Application No. 2019101716168, 1 page.
The State Intellectual Property Office of People's Republic, Second Office Action, Application No. 201910171616.8, dated Oct. 11, 2021, 5 pages.
The State of Intellectual Property of People's Republic of China, First Office Action, Application No. 201910171616.8, dated Jan. 29, 2021, 5 pages, English Translation Attached, 8 pages.
Zhou, Fanlin "A Pass for Beauty Salons" ISBN 978-7-5641-4615-3, Jan. 31, 2014, 2 pages.
Unknown, "General History of Chinese Culture" ISBN: 7-208-09030-9, Dec. 2010, 3 pages.
Written Opinion of the International Searching Authority, China National Intellectual Property Administration, Application No. PCT/CN2020/077895, dated May 28, 2020, 5 pages. English Translation Attached, 6 pages.
Unknown, "Listen to the Body" ISBN 978-7-5352-4287-7, 2009, 2 pages.

* cited by examiner

*Primary Examiner* — Eisa B Elhilo
(74) *Attorney, Agent, or Firm* — ZIEGLER IP LAW GROUP LLC

(57) ABSTRACT

Provided are indigo darkener, containing: in parts by weight, 0.1-99 of indigo dye, 0-99 of alkaline dyeing assistant, 0.01-99 of acidic dyeing assistant, and 0-99 of oxidizing agent, and hair dyeing process using the indigo darkener. The multi-layer scales on the surface of hair are opened at large angles under alkaline condition and/or high-temperature condition, so that large indigo dyeing particles are easily absorbed in the scales; black indigo oxocarbon or carbon black is generated under the action of alkaline dyeing assistant and oxidizing agent at high temperature by the property that the indigo dye is easy to oxidize; the acidic dye assistant is added as the temperature decreases, and the scales having opening angles on the surface of hair are closed under acidic condition, so that the indigo carbide is firmly clamped and fixed in the scales of hair; finally, the blue indigo dyes white hair into black.

7 Claims, No Drawings

INDIGO DARKENER AND HAIR DYEING PROCESS

The present application claims the priority of the Chinese patent application, filed with China Patent Office, entitled "Indigo Darkener and Hair Dyeing Process" with application No. 201910171616.8 on Mar. 7, 2019, which are incorporated in this application by reference in its entirety.

TECHNICAL FIELD

The present application relates to the technical field of hair dyeing, in particular to an indigo darkener and a hair dyeing process.

BACKGROUND Art

If the hair is not alkalized, the hair scales will be closed naturally. When the hair is alkalized at room temperature, the hair scales will be opened naturally, and only a small amount of plant indigo dye with large particle is embedded in the hair scales, many of which will fall off and dissolve in water after washing. A small amount of plant indigo hair dye can only dye the hair into light green, light blue or light purple. Even if dyed repeatedly for several times, the hair cannot be dyed into pure indigo, and it's even more impossible to dye white hair into black.

During the hair dyeing, indigo hair dyes, especially oxidized-type plant hair dyes, are only oxidized naturally and slowly under the air at room temperature to oxidize the plant indigo into invalid indigo pure powder of light green. Even if the oxidation proceeds with the time up to thousands of minutes, the hair can only be dyed into light green, light blue or light purple, not pure indigo, let alone pure black.

In order to dye white hair into black, when indigo hair dye is used, indigo plant hair dye is often adhered to the hair surface with adhesives such as dye-fixing agent, hair gel or egg white. In the case of color fixing and locking through physical methods, the hair is rinsed with clear water after dyeing, but almost all the adhesive will be washed away during washing. The remaining small amount of indigo will only dye the white hair into light blue, light green and light purple, not pure indigo, let alone pure black.

Therefore, the hair dye containing indigo in the prior art cannot effectively dye the white hair into dark and shiny hair due to insufficient pretreatment, difficult dyeing and color fixing or insufficient post-treatment, which can only obtain various other colors, affecting the black dyeing effect.

SUMMARY

The technical problem to be solved by the present application is to provide an indigo darkener. The indigo darkener provided by the present application can dye white hair into dark and shiny hair.

In view of this, the present application provides an indigo darkener, including:
indigo dye: 0.1-99 parts by weight;
alkaline dyeing assistant: 0-99 parts by weight;
acidic dyeing assistant: 0.01-99 parts by weight;
oxidizing agent: 0-99 parts by weight.

Preferably, the indigo darkener also includes 0.001-99 parts by weight of dyeing supplement.

Preferably, the indigo dye is selected from one or more of natural plant indigo dyes and synthetic indigo dyes; the natural plant indigo dye is made by fermentation of plant leaves containing indolic acid component, and the natural plant indigo dye is selected from one or more of plant indigo and plant indigo naturalis; the synthetic indigo dye is selected from one or more of food blue 1, food blue 2, brilliant blue, acidic indigo, hardened indigo, C.1. pigment blue 66, monolite navy blue BV, C.1. reduced blue 1,2,2-diazaindene indigo, indigo, pure indigo, indigo (1), Xian-ShaJianDing synthetic indigo/2, indigo powder, reduced indigo, indigosol and indigoidine; the indigo dye is other plant dyes that are easy to be oxidized to form carbon black or black carbon oxide;

the alkaline dyeing assistant is selected form one or more of organic alkali, inorganic alkali and other alkali substances with alkaline pH value;

the acidic dyeing assistant is selected from one or more of organic acids, inorganic acids and other acidic substances with acidic pH value; and the oxidizing agent is selected from one or more of organic oxidizing agent, inorganic oxidizing agent, neutral oxidizing agent and other oxidizing substances with oxidation effect.

Preferably, the dyeing supplement is selected from one or more of camphire, madder, henna, Impatiens balsamina, mignonettetree, lawsonia inermis L, leaf of henna, Impatiens balsamina L, amaranth, Syzygium aromaticum, Morus nigra, mulberry, sorosis, hispid arthraxon, Perillae Fructus, common bletilla tuber, indigotin, Algal lotus, radix lithospermi, sapanwood, hematoxylin, indigo, Carthamus tinctorious, punicagranatum, Gardenia jasminoides Ellis, Fructus Gardeniae, Artemisia argyi, rheum officinale, the fruit of Chinese magnoliavine, isatis root, blue grass, jiangjin, Flos Sophorae Immaturus, Rhamnus utilis, shell of an acorn, chinese sapium, Chinese gall, acorn shell, chestnut rind, lotus seed shell, persimmon, alums, avocado fruit, Polygonum multiflorum, sappan lignum, dye yam, Excoecaria sebifera, Buchnera cruciatas Hamilt, Asiatic wormwood, Strobilanthes cusia, Polygonum tinctorium Ait., Isatis indigotica Fortune, purple perilla, Haematoxylum campechianum, red wine, coffee, tea, indigo naturalis, carbon black, conductex, beer, lemon and Chrysanthemum morifolium Ramat extract.

Preferably, the indigo darkener includes: 5-50 parts by weight of indigo dye, 1-80 parts by weight of alkaline dyeing assistant, 1-20 parts by weight of acidic dyeing assistant, and 1-40 parts by weight of oxidizing agent.

Or, the indigo darkener includes: 20-40 parts by weight of indigo dye, 2-20 parts by weight of alkaline dyeing assistant, 5-20 parts by weight of acidic dyeing assistant, and 2-10 parts by weight of oxidizing agent.

Preferably, the indigo darkener includes: 5-50 parts by weight of indigo dye, 5-50 parts by weight of alkaline dyeing assistant, 1-30 parts by weight of acidic dyeing assistant, 1-40 parts by weight of oxidizing agent, 0.05-40 parts by weight of dyeing supplement.

Or, the indigo darkener includes: 20-40 parts by weight of indigo dye, 5-10 parts by weight of alkaline dyeing assistant, 4-20 parts by weight of acidic dyeing assistant, 2-10 parts by weight of oxidizing agent, 0.5-20 parts by weight of dyeing supplement.

The present application also provides a hair dyeing process using the indigo darkener, including the following steps:

A) mixing 0-99 parts by weight of alkaline dyeing assistant with water, applying the obtained mixture on the hair, heating and keeping warm, and then rinsing with water, with the content of the alkaline dyeing assistant being not 0;

or, heating the hair at high temperature, with the content of the alkaline dyeing assistant being 0;

B) mixing 0.1-99 parts by weight of indigo dye with water, applying the obtained mixture on the hair obtained in step A), heating and keeping warm, and then rinsing with water;
C) mixing 0-99 parts by weight of oxidizing agent with water, applying the obtained mixture on the hair obtained in step B), heating and keeping warm, and then rinsing with water, with the content of the oxidizing agent being not 0;
or oxidizing the hair obtained in step B) naturally, with the content of the oxidizing agent being 0; and
D) mixing 0.01-99 parts by weight of acidic dyeing assistant with water, applying the obtained mixture on the hair obtained in step C), heating and keeping warm, and then rinsing with water.

Preferably, in step A) and/or step B), the mixture also includes 0.001-99 parts by weight of dyeing supplement.

Preferably, the process also includes after step B):
B') mixing 0.001-99 parts by weight of dyeing supplement with water, applying the obtained mixture on the hair obtained in step B), heating and keeping warm, and then rinsing with water.

Preferably, when the content of the oxidizing agent is not 0, the process also includes after step B) and before step B'):
B") natural oxidizing the hair obtained in step B), wherein the natural oxidation is oxidation in the air, blowing hot air or sun exposure.

The present application provides an indigo darkener, including: 0.1-99 parts by weight of an indigo dye, 0-99 parts by weight of an alkaline dyeing assistant, 0.01-99 parts by weight of an acidic dyeing assistant, and 0-99 parts by weight of an oxidizing agent. In the process of dyeing white hair into black hair, the hair scales will be opened naturally when the hair is at high temperature, so that plant indigo dye particles of large particle would be embedded in the scales; some indigo dyeing particles are oxidized at high temperature to produce black carbon oxides due to such natural property that plant indigo is not heat-resistant and easy to be oxidized in the air at high temperature, so that white hair can be dyed into blue gray hair; the scales on the surface of the hair will be closed by the acidic dyeing assistant, and the black carbon oxide of indigo and carbon black (C) are firmly clamped in the scales of the hair, so that the dyeing fastness of the indigo darkener can be comparable to that of a chemical hair dye. In addition, due to the closure of the scales on the hair surface, the hair surface presents a smooth effect, resulting in high fish-scale-like brightness, which will make the dyed black hair dark and shiny.

Further, multi-layer scales on the surface of the hair are opened at large angles when the alkaline dyeing assistant contained in the indigo darkener is under high-temperature condition, so that large indigo dyeing particles would be absorbed in the scales in a larger amount; at the same time, the hydroxyl ion of the alkaline dyeing assistant has a strong adsorption with many carboxyl and amino groups on the surface of hair fiber, resulting in the alkaline dyeing assistant implanted in the surface layer or scale of hair, which is difficult to be washed off by water; meanwhile, carbon oxide produced by the indigo dye, due to its activity, can forms water-insoluble ion groups with metal ions, hydroxyl ions and acid ions contained in the alkaline dyeing assistant, and such water-insoluble ion groups have hydrolysis resistance, so as to be firmly adsorbed and precipitated on the hair surface and in the scales to prevent falling off by washing during or after dyeing; at high temperature, the hydrate of alkaline dyeing assistant is easy to produce metal secondary oxide that continues to be oxidized to form peroxide which has oxidability to indigo dyeing particles, so that more indigo dyes are oxidized to form carbon oxide with the color of carbon black, thus dyeing white hair into pure black hair. In order to increase the oxidation rate and carbonization rate of indigo, in high temperature condition, almost all of the indigo dyeing particles are violently oxidized and carbonized to produce carbon black (C) by oxidizing agent, so white hair can be completely dyed into dark black hair.

Further, black hair with different color light styles can be obtained by adding a dyeing supplement during the dyeing.

The results show that after applying the indigo darkener according to the present application, the chromaticity of the dyed black hair can reach degree 1 of the international standard chromaticity of dyed hair; the dyeing fastness is up to grade 5 of the international textile fiber dyeing fastness standard; the glossiness of dyed hair is up to greater than 70 GU.

DETAILED DESCRIPTION

In order to further understand the present application, the preferred embodiments of the application are described below in combination with the Examples, but it should be understood that these descriptions are only for further explaining the features and advantages of the application, rather than limiting the claims of the application.

In view of the current situation that the indigo darkener in the prior art cannot dye white hair into black hair, the present application provides an indigo darkener, containing specific components of indigo dye, alkaline dyeing assistant, acidic dyeing assistant, and oxidizing agent. In the present application, by adding the above components, the indigo darkener can dye white hair into black and shiny hair, with the chromaticity of the dyed black hair reaching degree 1 of the international standard chromaticity of dyed hair, the dyeing fastness of the dyed black hair being up to grade 5 of the international textile fiber dyeing fastness standard, and the glossiness of the dyed black hair being>70 GU. Specifically, the indigo darkener described in the present application includes:
indigo dye: 0.1-99 parts by weight;
alkaline dyeing assistant: 0-99 parts by weight;
acidic dyeing assistant: 0.01-99 parts by weight; and
oxidizing agent: 0-99 parts by weight.

The indigo dye described in the present application is a dye well known to those skilled in the art, and its source is not particularly limited in the application; specifically, the indigo dye is selected from one or more of natural plant indigo dyes and synthetic indigo dyes; more specifically, the indigo dye is an organic blue dye plant indigo powder made by fermentation of one or more plant leaves containing indolic acid component, such as Polygonum tinctorium Ait., Isatis indigotica Fortune, Indigofera tinctoria L. and Strobilanthes cusia, including one or more of plant indigo and plant indigo naturalis; at the same time, the synthetic indigo dye is selected from one or more of synthetic food blue 1, food blue 2, brilliant blue, acidic indigo, hardened indigo, C1 pigment blue 66, monolite navy blue BV, C1 reduced blue 1,2,2-diazaindene indigo, indigo, pure indigo, indigo (1), XianShaJianDing synthetic indigo/2, indigo powder, indigo-blue powder, reduced indigo, indigosol and indigoidine; the indigo dye is also selected from other plant dyes that are easy to be oxidized to form carbon black (C) or black carbon oxide. In the present application, the content of the indigo dye is 0.1-99 parts by weight. In a specific example, the content of the indigo dye is 1-70 parts by weight. More specifically, the content of the indigo dye is 5-50 parts by weight. More specifically, the content of the indigo dye is 20-40 parts by weight.

The component of indigo in the indigo dye has natural property that is easy to be oxidized. The oxidation of indigo can be divided into slow oxidation at room temperature and acute oxidation at high temperature, as well as slow oxidation in the air at room temperature and strong oxidation at high temperature with oxidant. In the case of acute oxidation at high temperature, indigo dyes are mostly oxidized to generate black carbon oxides; almost all indigo dyeing particles after strong oxidation at high temperature produce carbon black (C). In order to increase the oxidation rate of indigo and the carbonization ratio of indigo, on the one hand, the oxidation rate can be increased through increasing the temperature, and at the same time, the carbonization ratio can be improved by using oxidant at high temperature, so as to obtain more carbon black (C) or black carbon oxide, thus promoting white hair to be dyed into pure black hair.

The alkaline dyeing assistant contained in the indigo darkener is selected form one or more of organic alkali (base) and inorganic alkali; more specifically, the alkaline dyeing assistant is selected from one or more of hydrated lime, quicklime, lime water, sodium thiosulfate, soda, soda ash, sodium carbonate, sodium bicarbonate, sodium hydroxide, ammonium hydroxide, barium hydroxide, calcium hydroxide, cobalt hydroxide, potassium hydroxide, potassium carbonate, potassium bicarbonate, potash, potassium sulfate, potassium chloride, lithium hydroxide, aluminum hydroxide, magnesium hydroxide, strontium hydroxide, iron hydroxide, copper hydroxide, iron hydroxide, ferrous hydroxide, sodium methoxide, ammonium mercaptoacetate, leonurine, theophyllinum, trona, sodium carbonate, potassium carbonate, bitter fleabane, Halogeton arachnoideus, pottasche, fleabane ash, small ash, large ash, plant ash, winter reed ash, sunflower ash, mulberry ash, plant ash, and other alkali substances with alkaline pH value; more preferably, alkali substances which can form an basic salt insoluble in water with indigo. The content of the alkaline dyeing assistant is 0-99 parts by weight; in a specific example, the content of the alkaline dyeing assistant is 1-80 parts by weight; more specifically, the content of the alkaline dyeing assistant is 1-50 parts by weight, more specifically, the content of the alkaline dyeing assistant is 2-20 parts by weight.

The scales of hair are opened naturally under the condition of high temperature. Further, since the hair fibers are expanded under alkaline conditions with the aid of the alkaline dyeing assistant, surface scales are opened at large angles, so that large indigo dyeing particles would be can be embedded in the scales having large opening angles for preparation before dyeing. At the same time, the alkaline dyeing assistant has alkalinity, and its hydroxyl (OH) can form chemical bonds with carboxyl and amino groups of hair, so that the alkaline dyeing assistant can be firmly implanted into the surface layer and scales of hair, which is not easy to be washed off. In addition, the pH value of originally acidic hair can become alkaline, so as to meet the natural properties that the plant indigo can be dyed under alkaline conditions. Meanwhile, during dyeing, indigo can be oxidized to produce carbon oxide of indigo by using the peroxide decomposed by the metal secondary oxide produced by the alkaline dyeing assistant at high temperature. Carbon oxide of indigo has activity, which can form the water-insoluble basic salt with the ion of hydrate of alkaline dyeing assistant, so that indigo can be adsorbed and precipitated in the hair surface and scales, so as to improve the adsorptive and embedded fastness of large indigo dyeing particles, thus preventing it from falling off by washing after dyeing.

The indigo darkener according to the present application also includes an oxidizing agent, which can be one or more of organic oxidizing agent and inorganic oxidizing agent; specifically, acidic oxidizing agent in the oxidizing agent is selected from one or more of hydrogen peroxide, perhydrol, peroxyacetic acid, sodium dichromate, chromic acid-nitric acid, potassium permanganate, purplesalt and ammonium persulfate; the alkaline oxidizing agent is selected from one or more of sodium hypochlorite, sodium dichloroisocyanurate, sodium percarbonate, sodium perborate, potassium perborate and other oxidizing substances with oxidation; the neutral oxidizing agent is selected from one or more of bromine, iodine, oxygen, air, mixture of oxygen and air, and hydrate of oxygen and water. The content of the oxidizing agent is 0-99 parts by weight. In a specific example, the content of the oxidizing agent is 0.8-80 parts by weight. More specifically, the content of the oxidizing agent is 1-40 parts by weight. More specifically, the content of the oxidizing agent is 2-10 parts by weight.

Plant indigo dye has natural property that is easy to be oxidized. The indigo is acutely oxidized through the strong oxidation of the oxidizing agent at a high temperature. After acutely oxidized, almost all of the indigo is sub-burned to generate carbon black (C), so that the original blue indigo dye generates black indigo carbon black (C), so as to dye white hair into black hair.

The acidic dyeing assistant is selected from one or more organic acids and inorganic acids; more specifically, the acidic dyeing assistant is selected from one or more carbonic acid, phosphoric acid, sulfuric acid, hydrochloric acid, sulfonic acid, sulfinic acid, citric acid, oxalic acid, fruit acid, formic acid, acetic acid, edible vinegar, edible acetin, and other acidic substances with acidic pH value. The content of the acidic dyeing assistant is 0.01-99 parts by weight; in a specific example, the content of the acidic dyeing assistant is 0.5-70 parts by weight; more specifically, the content of the acidic dyeing assistant is 1-20 parts by weight; more specifically, the content of the acidic dyeing assistant is 5-20 parts by weight.

Under acidic conditions, hair fibers are tightened and scales are closed. Thus, an acidic dyeing assistant is added to close the hair scales, and then the indigo dye particles adsorbed and precipitated in the hair scales are clamped therebetween to form a permanent embedment, so as to increase the dyeing fastness. Due to the closure of the scales on the hair surface, the hair surface presents a smooth effect, resulting in high fish-scale-like brightness, which will make the dyed black hair dark and shiny, thereby increasing glossiness of dyed hair.

In the present application, the indigo darkener also contains dyeing supplement, and the dyeing supplement is selected from one or more of camphire, madder, henna, Impatiens balsamina, mignonettetree, lawsonia inermis L, leaf of henna, Impatiens balsamina L, amaranth, Syzygium aromaticum, Morus nigra, mulberry, sorosis, hispid arthraxon, Perillae Fructus, common bletilla tuber, indigotin, Algal lotus, radix lithospermi, sapanwood, hematoxylin, indigo, Carthamus tinctorious, punicagranatum, Gardenia jasminoides Ellis, Fructus Gardeniae, Artemisia argyi, rheum officinale, the fruit of Chinese magnoliavine, isatis root, blue grass, jiangjin, Flos Sophorae Immaturus, Rhamnus utilis, shell of an acorn, chinese sapium, Chinese gall, acorn shell, chestnut rind, lotus seed shell, persimmon, alums, avocado fruit, Polygonum multiflorum, sappan lignum, dye yam, Excoecaria sebifera, Buchnera cruciatas Hamilt, Asiatic wormwood, Strobilanthes cusia, Polygonum tinctorium Ait., Isatis indigotica Fortune, purple perilla, Haematoxylum campechianum, red wine, coffee, tea, indigo naturalis, carbon black, conductex, beer, lemon and Chrysanthemum morifolium Ramat extract. The content of the dyeing supplement is 0.01-99 parts by weight; in a specific example, the content of the dyeing supplement is 0.03-70 parts by weight; specifically, the content of the dyeing supplement is 0.05-40 parts by weight; more specifically, the content of the dyeing supplement is 0.5-20 parts by weight.

The dyeing supplement can further improve the black dyeing effect of the indigo dye; or, after the hair is dyed black with the indigo dye, the dyeing supplement is used for dyeing black with different color light styles.

The present application also provides a hair dyeing process by using the above indigo darkener, including the following steps:

A) mixing 0-99 parts by weight of alkaline dyeing assistant with water, applying the obtained mixture on the hair, heating and keeping warm, and then rinsing with water, with the content of the alkaline dyeing assistant being not 0; or, heating the hair at high temperature, with the content of the alkaline dyeing assistant being 0;

B) mixing 0.1-99 parts by weight of indigo dye with water, applying the obtained mixture on the hair obtained in step A), heating and keeping warm, and then rinsing with water;

C) mixing 0-99 parts by weight of oxidizing agent with water, applying the obtained mixture on the hair obtained in step B), heating and keeping warm, and then rinsing with water, with the content of the oxidizing agent being not 0; or oxidizing the hair obtained in step B) naturally, with the content of the oxidizing agent being 0; and D) mixing 0.01-99 parts by weight of acidic dyeing assistant with water, applying the obtained mixture on the hair obtained in step C), heating and keeping warm, and then rinsing with water.

In the above hair dyeing process, in order to dye the hair smoothly, the alkaline dyeing assistant, indigo dye, oxidizing agent, acidic dyeing assistant and dyeing supplement can be prepared in advance, or the above components can be prepared during hair dyeing.

Firstly, the hair surface layer is the outermost layer of the hair, which is usually composed of 2-4 layers of scales. The surface layer is usually translucent or colorless and transparent, so the natural hair color or dyed hair color can be shown. The hair has a pH value of between 4.5 and 5.5. With the increase of temperature and pH value, the alkalinity increases, and the surface layer of hair will be expanded, divided and the scales will be opened. With the continuous increase of pH value and temperature and the extension of heating time, opening angles of the scales will continue to increase, and the hair will become fluffy and rough, which is the porosity of hair. Therefore, using the natural property of the hair, the hair is subjected to an alkaline treatment before dyeing with an indigo dye, so that the scales of hair surface are opened at a maximum angle to form a porous structure, which is convenient for the adsorption of large indigo dye particles into the scales. At the same time, the alkaline dyeing assistant is also an alkaline pH regulator. Therefore, firstly, 0-99 parts by weight of alkaline dyeing assistant is mixed with water, the obtained mixture is applied on the hair, heating and keeping warm followed by rinsing with water; in this process, the temperature of water is 0-100° C., and the pH of the mixture after mixing the alkaline dyeing assistant with water is 7-14; the heating temperature is 0-100° C. and the time for keeping warm is 1-1200 min. In a specific example, the heating temperature is 35-70° C. and the time for keeping warm is 10-60 min.

In the present application, high temperature dyeing can be directly carried out by using the indigo dye without the above steps according to the actual hair dyeing and hair quality requirements.

The technological conditions, steps, raw materials and contents of the indigo darkener in the application are also applicable to other plant dyes used to dye different colors of hair.

According to the present application, the dyeing process of indigo dye is carried out after an alkaline treatment with alkaline dyeing assistant, specifically: mixing 0.1-99 parts by weight of indigo dye with water, and applying the obtained mixture on the hair obtained in step A), heating and keeping warm followed by rinsing with water; in above process, the temperature of water is 0-100° C., and the pH of the mixture after mixing the indigo dye with water is 7-14; the heating temperature is 0-100° C. and the time for keeping warm is 1-1200 min. In a specific example, the heating temperature is 30-85° C. and the time for keeping warm is 10-70 min.

In the present application, an alkaline treatment with alkaline dyeing assistant is carried out before the dyeing treatment. This process has the mechanism specifically as follows.

There is a thin and transparent layer of keratinized cells on the surface of the hair, and these keratinized cells overlap with each other as roof tiles, which is traditionally called as scutella. The scutella contain a variety of long chain molecules of α-amino acids, on which are rich in carboxyl, amino and hydroxyl groups, and salt bonds, hydrogen bonds, disulfide bonds and ammonia bonds are formed between molecules. The carboxyl and amino groups on the surface of the hair have excellent attraction and adsorption with alkaline substances having hydroxyl radical. Using the natural property of the hair, the hair is subjected to the alkaline treatment before dyeing with indigo dye, and the surface layer and scales of the hair are implanted with the alkaline dyeing assistant with hydroxyl radical. The alkaline dyeing assistant is combined with indigo or its carbon oxide to form a water-insoluble basic salt. This ionic group composed of metal ions, hydroxyl ions, acid ions and indigo carbon oxide ions is resistant to hydrolysis, so that the indigo or black indigo carbon oxide is firmly combined with the hair, which has relatively high water washing fastness and rubbing fastness, thus preventing from being washed off during dyeing. The alkaline dyeing assistant is also a good alkaline pH regulator. At the same time, the alkaline dyeing assistant has degreasing effect, and thus the problem of hydrophobicity on the surface of oily hair can be solved, resulting in a close combination of the indigo dye with the hair. In addition, the alkaline dyeing assistant has the function of bleaching and decolorization to remove the variegation on the hair, so as to obtain the pure black hair.

For example, the alkaline treatment is carried out by using hydrated lime (quicklime) as an alkaline agent based on the following mechanism: $Ca(OH)_2$ is implanted into the surface layer or scales of the hair by using the strong adsorption between many carboxyl and amino groups on surface of the hair fiber with OH radical of hydrated lime $Ca(OH)_2$, quicklime CaO or its hydrate lime water. Indigo or its carbon oxide is subjected to calcification with $Ca(OH)_2$ at a high temperature to produce a calcium compound of indigo-$CaCO_3$ that is insoluble in water, which is firmly adsorbed and precipitated on the hair surface and inside scales, so as to solidify indigo and indigo carbon oxide. At the same time, hydrated lime (quicklime) has the function of degreasing and bleaching, which can bleach other pigments affecting hair blackening, and thus dyeing white hair into pure black.

According to the natural property that the indigo dye is easy to be oxidized, a small amount of indigo will form black carbon oxide after it is oxidized by air in the process of high temperature dyeing. Also, the hydrate of alkaline dyeing assistant has strong adsorption with many carboxyl groups on the surface of the hair fiber, so that it will be absorbed on the hair surface and inside scales. Alkaline hydrate is easy to produce metal secondary oxide at a high temperature, which is unstable with the increase of temperature and thus continues to be oxidized to form oxide and peroxide. Since this peroxide has oxidizability, a large amount of indigo is oxidized to form black carbon oxide; for example, sodium carbonate can decompose into sodium oxide and carbon dioxide at a high temperature: $Na_2CO_3=Na_2O+CO_2\uparrow$; sodium oxide can be oxidized to produce sodium peroxide under heating conditions: $2Na_2O+O_2=2Na_2O_2$, sodium peroxide has oxidizability.

After the completion of the above dyeing, if the black dyeing effect is further improved or the black hair is required to have the black dyeing effect of different color light styles, supplementary dyeing can be carried out. In the present application, the dyeing supplement for supplementary dyeing can be used together with the indigo hair dye in the hair dyeing process; the dyeing supplement can also exist in the dyeing process of the alkaline dyeing assistant, and can also be supplemented separately after the hair dyeing is completed. The specific situation is as follows:
mixing 0.001-99 parts by weight of dyeing supplement with water, and applying the obtained mixture on the hair obtained after hair dyeing, heating and keeping warm followed by rinsing with water.

In the above supplementary dyeing process, the temperature of water is 0-100° C., the pH of the mixture obtained after mixing the dyeing supplement with water is 7-14, the heating temperature is 0-100° C., and the time for keeping warm is 1-1200 min; in a specific example, the heating temperature is 20-70° C. and the time for keeping warm is 70-120 min.

In the present application, an oxidation treatment is then carried out. In the case of adding the oxidizing agent, the oxidation process is specifically as follows: mixing the oxidizing agent with water, and apply the obtained mixture on the dyed hair, heating and keeping warm followed by rinsing with water; in this process, the temperature of water is 0-100° C., the heating temperature is 0-100° C., and the time for keeping warm is 1-1200 min; in a specific example, the heating temperature is 30-70° C. and the time for keeping warm is 10-80 min.

The indigo is highly carbonized in the above oxidation process of the oxidizing agent based on the following specific mechanism: the indigo dye has poor heat resistance, light resistance, alkali resistance, oxidation resistance, salt resistance and bacterial resistance; when the indigo powder is placed in the air, it will soon be oxidized and invalid, and will be oxidized quickly by the heating and light, which is unstable to citric acid, tartaric acid and alkali.

In order to further accelerate the oxidation rate of the indigo and improve the carbonization ratio of the indigo, it can also be used that the indigo will be strongly oxidized by the oxidizing agent at a high temperature. Since the indigo dye is an organic matter composed of carbon, oxygen and hydrogen, almost all the indigo after strong oxidation generates carbon black (C), and the carbonized indigo loses its original blue and turns into black.

In the case of without adding oxidizing agent, if the requirement for dyeing blackness is not high, natural oxidation can be carried out; the natural oxidation can be the form of slow oxidation in the air, or the oxidation speed can be improved by blowing hot air or sun exposure. According to specific conditions, the above natural oxidation can be carried out after hair dyeing and before oxidation with the oxidizing agent; it can also be carried out after acidification treatment.

According to the present application, the hair is finally subjected to an acid treatment, which is specifically as follows: mixing 0.01-99 parts by weight of the acidic dyeing assistant with water, and applying the obtained mixture on the hair obtained in step C), heating and keeping warm followed by rinsing with water; the temperature of water is 0-100° C., the pH of the mixture obtained by mixing the acidic dyeing assistant with water is 1-7, the heating temperature is 0-100° C., and the time for keeping warm is 1-1200 min; the heating temperature is 30-60° C. and the time for keeping warm is 10-60 min.

In the present application, the acidification treatment with the acidic dyeing assistant is finally carried out based on the following mechanism: the surface layer of the hair is a scale layer, which grows along a certain direction from the hair root to the hair tip. Each scale is connected with the cortical layer at one end of the hair root, and the other end is opened outward. The scales are covered and connected one by one. Scales have a large covering density on the hair, 3-4 layers of scales cover on the hair, mostly presenting a corrugated form and fish scale-like. The scales on the surface of normal hair overlap and cover each other, making the appearance of hair bright and smooth. The pH value of hair is 4.5-5.5 under normal condition, which is acidic. Under alkaline conditions, the hair surface will be opened, divided, and thus the hair will become fluffy and porous. In case of exposure of an acid, the scales on the surface layer will be closed naturally, and the hair surface layer turns back to the original dense and smooth, with luster. If the dyed hair is not acidified, the opened hair scales are not closed naturally, and the surface of hair fibers becomes rough, resulting in a diffuse reflection effect of light, which makes the hair lose its original natural luster, and the dyed hair will appear charred black. According to the present application, the scales on the hair surface has the natural property of being opened in alkali and closed in acid, and thus when a large number of indigo pigment particles are gathered in the scales on the hair surface after the completion of indigo dyeing, the hair is subjected to the acidification treatment with the acidic dyeing assistant, resulting in that the indigo is firmly clamped and fixed after the scales are closed, and the carbonized indigo appears charcoal black, showing a black hair through the transparent corneum. Due to the closure of scales on the hair surface, the hair surface presents a smooth effect, resulting in high fish-scale-like brightness, which will make the dyed hair black and bright. At the same time, the acidic dyeing assistant can also adjust the acid pH value, so that the pH value of the dyed hair can be restored to the safe value of the human surface of 4.5-5.5.

In the specific example, the present application can obtain the following conclusions after actual hair dyeing: the indigo darkener includes 5-50 parts by weight of indigo dye, 1-80 parts by weight of alkaline dyeing assistant, 1-20 parts by weight of acidic dyeing assistant, and 1-40 parts by weight of oxidizing agent. The above indigo darkener can dye white hair into black hair with the chromaticity reaching degree 2-3 of the international standard chromaticity of dyed hair, i.e. natural black or dark brown black, specifically reaching the international oriental black hair standard or European black brown hair standard. The dyeing fastness of washing and sunlight can reach grade 4-5 of the international textile fiber dyeing fastness standard; specifically, the dyed hair will not fade or fade slightly after washing, and will not fade or fade slightly in the sun-exposure. The glossiness of the dyed hair is 50-70 GU, specifically reaching sub-lustrous or high lustrous (luminosity).

More preferably, the indigo darkener includes 20-40 parts by weight of indigo dye, 2-20 parts by weight of alkaline dyeing assistant, 5-20 parts by weight of acidic dyeing assistant, and 2-10 parts by weight of oxidizing agent. The above indigo darkener can dye white hair into dark black hair with the chromaticity of dyed hair reaching degree 1 of the international standard chromaticity of dyed hair, namely, international deeply black, specifically reaching the black hair standard of African black people. The dyeing fastness of washing and sunlight can reach grade 5 of the international textile fiber dyeing fastness standard; specifically, the dyed hair will not fade after washing, and will not fade in the sun-exposure. The glossiness of dyed hair is greater than 70 GU, specifically reaching high lustrous.

In the case of the indigo darkener including an dyeing supplement, the indigo darkener includes 5-50 parts by weight of indigo dye, 5-50 parts by weight of alkaline dyeing assistant, 1-30 parts by weight of acidic dyeing assistant, 1-40 parts by weight of oxidizing agent, and 0.05-40 parts by weight of dyeing supplement. The above indigo darkener can dye white hair into pure black hair or colored black hair with the chromaticity of dyed hair reaching degree 2-3 of the international standard chromaticity of dyed hair, namely, natural black or dark brown black, specifically reaching international oriental black hair standard or European black brown hair standard. The dyeing fastness of washing and sunlight can reach grade 4-5 of the international textile fiber dyeing fastness standard; specifically, the dyed hair will not fade or fade slightly after washing, and will not fade or fade slightly in the sun-exposure. The glossiness of dyed hair is 50-70 GU, specifically reaching sub-lustrous or high lustrous.

More preferably, the indigo darkener includes 20-40 parts by weight of indigo dye, 5-10 parts by weight of alkaline dyeing assistant, 4-20 parts by weight of acidic dyeing assistant, 2-10 parts by weight of oxidizing agent, and 0.5-20 parts by weight of dyeing supplement. The above indigo darkener can dye white hair into dark pure black hair or dark colored black hair with the chromaticity of dyed hair reaching degree 1 of the international standard chromaticity of dyed hair, namely, international deeply black, specifically reaching the black hair standard of African black people. The dyeing fastness of washing and sunlight can reach grade 5 of the international textile fiber dyeing fastness standard; specifically, the dyed hair will not fade after washing, and will not fade in the sun-exposure. The glossiness of dyeing is greater than 70 GU, specifically reaching high lustrous.

The indigo darkener provided by the present application breaks through the limitation that plant indigo can only dye into blue hair or can only be used as a complementary color for other plant darkeners, and also breaks through the limitations of poor dyeing fastness and poor dyeing luster of plant hair dye. Therefore, the present application provides an indigo darkener and a hair dyeing process, which realizes the technology of dyeing into black hair with plant indigo hair dye, and at the same time has the dyeing fastness and glossiness to which the traditional plant hair dye cannot be comparable. The present application provides people with a plant hair dye with pure natural elements, which is harmless to, non-toxic to human body, no primary irritation to skin and no skin allergy. It can directly dye white hair into black hair and has the chromaticity, dyeing fastness and glossiness comparable to those of a chemical hair dye.

In order to further understand the present application, the indigo hair dye and hair dyeing process provided by the application are described in detail below in combination with the examples. The protection scope of the application is not limited by the following examples.

In the following examples, the chromaticity, glossiness and dyeing fastness of the hair are evaluated specifically in the following manner:

the international chromaticity of the hair is 0 to 10; chromaticity is an indicator that is used to indicate the amount of melanin in the hair, and different chromaticities show different depths of the hair color; generally speaking, the color of the hair is classified into 10 chromaticities, which are represented by ten numbers from 1 to 10, respectively; the smaller the number is, the higher the melanin content is and the darker the color is; on the contrary, the larger the number is, the less the melanin content is and the lighter the color is. The specific standards are: 1-dark black, 2-natural black, 3-dark brown, 4-brown, 5-light brown, 6-dark gold, 7-gold, 8-light gold, 9-lighter gold and 10-very light gold.

Chinese hair has generally the chromaticity that is degree 1-3, and the most common is degree 2, which is also known as natural black; African black hair has the chromaticity that is generally degree 1, which is also known as dark black; European hair has generally the chromaticity that is degree 4-6, in which degree 4 is also called as brown.

National standard glossiness: high glossiness>70 GU (high gloss); medium glossiness 10-70 GU (matte); low glossiness<10 GU (extinction).

International standard for dyeing fastness: the dyeing fastness is generally classified into five grades, including soaping, rubbing, perspiration and other fastness. Grade 1 is the worst and grade 5 is the best. The sunlight fastness and climate fastness are classified into eight grades, grade 1 is the worst and grade 8 is the best.

EXAMPLE 1

1) 50 g of sodium carbonate $Na_2CO_3$ was prepared into a solution having pH of 10 by using 100 g of clear water at 20° C., and then the solution was evenly applied on the hair, heating to 50° C. with a bath cap and electric heating cap, keeping warm for 120 minutes, and stopping heating;

2) 160 g of plant indigo was prepared into a slurry with 100 g of hot water of 80° C., and then the slurry was evenly applied on the hair coated with sodium carbonate, heating to 90° C. with a bath cap and electric heating cap under the condition of pH 10, keeping warm for 60 minutes, and stopping heating;

3) 40 g of sodium perborate was diluted into an aqueous solution with 300 g of clear water of 20° C., and then the aqueous solution was evenly applied on the hair coated with sodium carbonate and plant indigo powder, heating at 80° C. with a bath cap and electric heating cap, keeping warm for 40 minutes, and stopping heating;

4) 90 g of oxalic acid was diluted into an aqueous solution having pH of 3 by using 200 g of clear water of 35° C., and then the solution was evenly applied on the hair coated with sodium carbonate, plant indigo powder and sodium perborate, heating at 50° C. with a bath cap and electric heating cap, keeping warm for 20 minutes, after that, stopping heating, the hair was washed with clear water of 20° C. Thus, the white hair was dyed into pure black hair.

The chromaticity of dyed black hair can reach degree 1 of the international standard chromaticity of dyed hair; that is, the content of melanin is equivalent to the international chromaticity standard of dark black. The dyeing fastness of washing and sunlight can reach grade 4-5 of the international textile fiber dyeing fastness standard; that is, the dyed hair will not fade after washing, and will not fade in the sun-exposure. The glossiness of the dyed hair is greater than 50 GU, i.e. close to high lustrous.

EXAMPLE 2

1) Preparing an alkaline treatment agent: 100 g of hydrated lime $Ca(OH)_2$ powder was weighed in proportion, and mixed and dissolved in 500 g of water at room temperature to obtain a solution having pH of 14, that is, aqueous solution of alkaline treatment agent and hydrated lime $Ca(OH)_2$;
preparing indigo dyeing solution: 150 g of plant indigo naturalis powder was weighed in proportion and dissolved in 100 g of clear water of 40° C. to obtain an indigo dyeing solution (the preparation of indigo dyeing solution is synchronized with hair dyeing, i.e. it is just prepared until use in order to prevent oxidation failure);
preparing oxidizing agent: 100 ml of oxygen was mixed with 500 ml of water at 20° C. to prepare a mixture of oxygen and water;
preparing acidic dyeing assistant: 60 g of acetic acid and 300 g of clear water were mixed at 20° C. to obtain an aqueous organic acetic acid solution with a pH of 3;
2) performing dyeing:
A. alkaline treatment: 500 g of the prepared hydrate of alkaline treatment agent and hydrated lime $Ca(OH)_2$ with a pH value of 14 was evenly applied on the hair to be dyed, and then the hair coated with alkaline treatment agent was equipped with a bath cap and heated to 80° C. for 30 minutes by using an electric heating cap, after that, stopping heating, the hair was rinsed with clear water of 30° 3;
B. dyeing: 150 g of the prepared indigo dyeing solution was diluted with 100 g of clear water of 60° C., and then the diluted solution was evenly applied on the hair to be dyed, which was treated with alkali, in the case of the hair treated by an alkaline treatment agent, the alkaline treatment agent was fixed on the hair due to the action of hydroxyl radical, and thus the pH value of the hair was alkaline at this time; in addition, the pH value of the hair was slightly lower because part of the alkaline treatment agent was dissolved by water washing, so it can meet the process conditions of plant indigo dyeing under alkaline conditions; the hair coated with indigo dyeing solution was equipped with a bath cap, and was heated to 80° C. for 40 minutes by using an electric heating cap, after that, stopping heating, the hair was rinsed with clear water of 30° C.;
C. oxidation treatment: 400 g of mixture of oxygen with water was evenly applied on the hair, and then the hair wearing a bath cap was heated to 60° C. by using an electric heating cap and the temperature was maintained for 10 minutes, after that, the hair was rinsed with clear water of 50° C.;
D. acidification treatment: 200 g of prepared aqueous acetic acid solution (acidic dyeing assistant) with a pH value of 2 was evenly applied on the hair having undergone oxidation treatment, maintaining at room temperature for 10 minutes and the hair was rinsed with clear water of 30° C.

The above example realizes the dyeing of white hair into pure black hair, wherein the chromaticity of dyed black hair can reach degree 1 of the international standard chromaticity of dyed hair; that is, dark black. The dyeing fastness can reach grade 4-5 of the international textile fiber dyeing fastness standard; that is, the dyed hair will not fade after washing, and will not fade in the sun-exposure. The glossiness of the dyed hair is greater than 50 GU, i.e. close to high lustrous.

EXAMPLE 3

1) 50 g of potassium carbonate $K_2CO_3$ was diluted into an aqueous solution having pH of 14 by using 100 g of clear water at 80° C., and then the solution was evenly applied on the hair, heating to 80° C. with a bath cap and electric heating cap, keeping warm for 40 minutes, after that, stopping heating, the hair was washed with clear water of 50° C.; $K_2CO_3$ is alkaline, which adjusted the acidic hair to alkaline, thus playing the role of pH regulator, and meeting the property of the indigo dyeing under alkaline conditions;
2) 100 g of plant indigo powder was mixed with 5 g of henna powder to obtain a mixture, which was dissolved in 100 g of clear water of 20° C. to form a slurry, and then the slurry was evenly applied on the hair with a pH value of 12, heating to 85° C. with a bath cap and electric heating cap, keeping warm for 50 minutes, after that, stopping heating, the hair was washed with clear water of 50° C.;
3) 40 g of citric acid was mixed with 20 g of hydrogen peroxide to obtain a mixed liquid which was diluted with 300 g of clear water of 20° C. to form a solution with a pH value of 2, and then the obtained solution was evenly applied on the hair, heating to 38° C. with a bath cap and electric heating cap, keeping warm for 60 minutes, after that, stopping heating, the hair was washed with clear water of 50° C. Thus, the white hair was dyed into brown black hair.

The chromaticity of dyed black hair can reach degree 1-2 of the international standard chromaticity of dyed hair; that is, dark black or brown black. The dyeing fastness can reach grade 4-5 of the international textile fiber dyeing fastness standard; that is, the dyed hair will not fade after washing, and will not fade in the sun-exposure. The glossiness of the dyed hair is greater than 50 GU, i.e. close to high lustrous.

EXAMPLE 4

1) 100 g of plant ash was mixed with 250 g of clear water to produce a paste with a pH value of 14, and then the obtained paste was evenly applied on the hair, heating to 70° C. with a bath cap and electric heating cap, keeping warm for 40 minutes, after that, stopping heating, the hair was washed with clear water of 35° C.;
2) 70 g of plant indigo was prepared into a slurry with 100 g of hot water of 50° C., and then the slurry was evenly applied on the hair, heating to 70° C. with a bath cap and electric heating cap under the condition of pH 10, keeping warm for 50 minutes, after that, stopping heating, the hair was washed with clear water of 35° C.;
3) 10 g of formic acid was diluted into an aqueous solution with 100 g of clear water of 20° C., and then the aqueous solution with a pH of 3 was evenly applied on the hair, heating to 70° C. with a bath cap and electric heating cap, keeping warm for 30 minutes, after that, stopping heating, the hair was washed to be clear with clear water of 35° C.;
4) since the indigo has a poor light resistance, the natural oxidation was carried out in a manner of sun-exposure oxidation by using the ultraviolet in sunlight and oxygen in the air. It took 600 minutes to dye the white hair into blue black hair.

The chromaticity of dyed black hair can reach degree 2 of the international standard chromaticity of dyed hair; that is, the content of melanin is equivalent to the natural black. The dyeing fastness of washing and sunlight can reach grade 4-5 of the international textile fiber dyeing fastness standard; that is, the dyed hair will not fade after washing, and will not fade in the sun-exposure. The glossiness of the dyed hair is greater than 50 GU, i.e. close to high lustrous.

EXAMPLE 5

1) 400 g of plant indigo powder was mixed with 300 g of clear water of 80° C. to form a slurry with a pH value of 7, and the obtained slurry was evenly applied on the hair, heating to 75° C. with a bath cap and electric heating cap, keeping warm for 60 minutes, the hair was washed with clear water of 50° C.;
2) 100 g of Gardenia jasminoides Ellis (plant dye) was mixed with clear water of 70 isxed with 300 g of clear water of 80° C. to form a slurry with a pH value of 7, and the obtaheated to 80° C. by using a bath cap and electric heating cap under the condition of a pH of 7, keeping warm for 60 minutes, stopping heating, the hair was washed with clear water of 50 of
3) 20 g of potassium hypermanganate was diluted with 200 g of clear water at 22° C. to form a solution which was evenly applied on the hair, heating at 60° C. with a bath cap and electric heating cap, keeping warm for 60 minutes, after that, stopping heating, the hair was washed with clear water of 50° C.;
4) 20 g of edible vinegar was dissolved in 100 g of clear water of 20° C. to form a solution with a pH value of 5, and the obtained solution was evenly applied on the hair, heating to 42° C. with a bath cap and electric heating cap, keeping warm for 60 minutes, after that, stopping heating, the hair was washed with clear water of 50° C. Thus, the white hair was dyed into blonde black hair.

The chromaticity of dyed black hair can reach degree 2-3 of the international standard chromaticity of dyed hair; that is, the content of melanin is equivalent to the international standard of natural black or dark brown. The dyeing fastness can reach grade 3-4 of the international textile fiber dyeing fastness standard; that is, the dyed hair will fade slightly after washing, and fade slightly in the sun-exposure. The glossiness of the dyed hair is greater than 70 GU, i.e. close to high lustrous.

EXAMPLE 6

1) 300 g of sunflower ash, 120 g of plant indigo powder, and 5 g of henna powder were mixed with 200 g of clear water of 20° C. to form a slurry with a pH value of 12, and then the obtained slurry was evenly applied on the hair, heating to 80° C. with a bath cap and electric heating cap, keeping warm for 50 minutes, the hair was washed with clear water of 30° C.;
2) 0.5 g of citric acid was diluted with 200 g of clear water of 20° C. to form a solution with a pH value of about 7, and then the obtained solution was evenly applied on the hair, heating to 40° C. with a bath cap and electric heating cap, keeping warm for 30 minutes, the hair was washed with clear water of 30° C.;
3) since the indigo has a poor oxidation resistance, the natural oxidation was carried out in air, and then the hair was dried and warmed by using a hot air blower for 20 minutes, then the white hair was dyed into black hair.

The chromaticity of dyed black hair can reach degree 2 of the international standard chromaticity of dyed hair; that is, the content of melanin is equivalent to natural black. The dyeing fastness of washing and sunlight can reach grade 3-4 of the international textile fiber dyeing fastness standard; that is, the dyed hair will fade slightly after washing, and fade slightly in the sun-exposure. The glossiness of the dyed hair is <50 GU, i.e. sub-lustrous.

EXAMPLE 7

The hair dyeing process was the same as that of Example 1, except that the following components were used: 50 g of plant indigo powder, 30 g of hematoxylin, 30 g of soda, 40 g of edible vinegar and 20 g of sodium percarbonate.

The chromaticity of dyed black hair can reach degree 2 of the international standard chromaticity of dyed hair. The dyeing fastness of washing and sunlight can reach grade 4-5 of the international textile fiber dyeing fastness standard. The glossiness of the dyed hair is greater than 50-70 GU.

EXAMPLE 8

The hair dyeing process was the same as that of Example 1, except that the following components were used: 800 g of brilliant blue, 750 g of soda ash, 820 g of fruit acid, and 890 g of potassium perborate.

The chromaticity of dyed black hair can reach degree 3 of the international standard chromaticity of dyed hair. The dyeing fastness of washing and sunlight can reach grade 4-5 of the international textile fiber dyeing fastness standard. The glossiness of the dyed hair is less than 50-70 GU.

EXAMPLE 9

The hair dyeing process was the same as that of Example 3, except that the following components were used: 100 g of indigo, 250 g of sodium methoxide, 300 g of sodium percarbonate, 10 g of citric acid, and 1 g of Syzygium aromaticum.

The chromaticity of dyed black hair can reach degree 2-3 of the international standard chromaticity of dyed hair. The dyeing fastness of washing and sunlight can reach grade 4-5 of the international textile fiber dyeing fastness standard. The glossiness of the dyed hair is less than 50-70 GU.

EXAMPLE 10

The hair dyeing process was the same as that of Example 3, except that the following components were used: 300 g of acidic indigo, 400 g of barium hydroxide, 380 g of hydrogen peroxide, 280 g of edible acetin, and 30 g of mulberry.

The chromaticity of dyed black hair can reach degree 2-3 of the international standard chromaticity of dyed hair. The dyeing fastness of washing and sunlight can reach grade 4-5 of the international textile fiber dyeing fastness standard. The glossiness of the dyed hair is less than 50-70 GU.

EXAMPLE 11

The hair dyeing process was the same as that of Example 1, except that the following components were used: 160 g of hardened indigo, 23 g of magnesium hydroxide, 180 g of carbonic acid, and 2 g of hydrogen peroxide.

The chromaticity of dyed black hair can reach degree 1 of the international standard chromaticity of dyed hair. The dyeing fastness of washing and sunlight can reach grade 5 of the international textile fiber dyeing fastness standard. The glossiness of the dyed hair is greater than 70 GU.

EXAMPLE 12

The hair dyeing process was the same as that of Example 1, except that the following components were used: 280 g of C1 pigment blue 66, 150 g of ammonium hydroxide, 180 g of acetic acid, and 20 g of peroxyacetic acid.

The chromaticity of dyed black hair can reach degree 1 of the international standard chromaticity of dyed hair. The dyeing fastness of washing and sunlight can reach grade 5 of the international textile fiber dyeing fastness standard. The glossiness of the dyed hair is greater than 70 GU.

EXAMPLE 13

The hair dyeing process was the same as that of Example 3, except that the following components were used: 200 g of indigosol, 100 g of sodium thiosulfate, 150 g of formic acid, 30 g of sodium hypochlorite, and 120 g of carbon black.

The chromaticity of dyed black hair can reach degree 1 of the international standard chromaticity of dyed hair. The dyeing fastness of washing and sunlight can reach grade 5 of the international textile fiber dyeing fastness standard. The glossiness of the dyed hair is greater than 70 GU.

EXAMPLE 14

The hair dyeing process was the same as that of Example 3, except that the following components were used: 150 g of food blue 2, 80 g of trona, 50 g of acetic acid, 20 g of peroxyacetic acid, and 150 g of lawsonia inermis L.

The chromaticity of dyed black hair can reach degree 1 of the international standard chromaticity of dyed hair. The dyeing fastness of washing and sunlight can reach grade 5 of the international textile fiber dyeing fastness standard. The glossiness of the dyed hair is greater than 70 GU.

COMPARATIVE EXAMPLE 1

1) 50 g of pottasche and 10 g of Carthamus tinctorious as dyeing supplement were mixed with 100 g of boiling water to form a paste with a pH value of 13, and then the obtained paste was evenly applied on the hair, heating to 80° C. with a bath cap and electric heating cap, keeping warm for 60 minutes, the hair was washed with clear water of 20° C.;
2) 300 g of plant indigo powder was mixed with 150 g of clear water of 40° C. to form a slurry, and then the obtained slurry was evenly applied on the hair with a pH value of 11, heating to 70° C. with a bath cap and electric heating cap, keeping warm for 120 minutes, the hair was washed with clear water of 20° C.;
3) 30 g of peroxyacetic acid was diluted into an aqueous solution with 200 g of clear water of 30° C., and then the obtained aqueous solution was evenly applied on the hair, heating to 70° C. with a bath cap and electric heating cap, keeping warm for 30 minutes, the hair was washed with clear water of 20° C. Thus, the white hair was dyed into charred black hair.

The chromaticity of dyed black hair can reach degree 1-2 of the international chromaticity of dyed hair; that is, the content of melanin is equivalent to the international standard of dark black or natural black. The dyeing fastness can reach grade 3-4 of the international textile fiber dyeing fastness standard; that is, the dyed hair will fade slightly after washing, and will fade slightly in the sun-exposure. The glossiness of the dyed hair is <50 GU, i.e. sub-lustrous.

COMPARATIVE EXAMPLE 2

1) 300 g of Polygonum tinctorium Ait. plant powder was mixed with 200 g of clear water of 30° C. to form a slurry, and then the obtained slurry was evenly applied on the hair, heating to 95° C. with a bath cap and electric heating cap under the condition of pH 7, keeping warm for 60 minutes, after that, stopping heating, the hair was washed with clear water of 40° C.;
2) since the indigo dye has a poor light resistance, the natural oxidation was carried out in a manner of sun-exposure oxidation by using the ultraviolet in sunlight and oxygen in the air, with time being 1200 minutes;
3) the hair was washed with 20 g of ordinary shampoo and clean water of 40° C. to dye the white hair into gray black hair.

The chromaticity of dyed black hair can reach degree 3-4 of the international standard chromaticity of dyed hair; that is, the content of melanin is equivalent to the international standard of dark brown or brown. The dyeing fastness of washing and sunlight can reach grade 3-4 of the international textile fiber dyeing fastness standard; that is, the dyed hair will fade after washing, and will fade in the sun-exposure. The glossiness of the dyed hair is <50 GU, i.e. sub-lustrous.

COMPARATIVE EXAMPLE 3

1) 100 g of potash was dissolved with 200 g of clear water of 20° C. to form an aqueous solution with pH value of 14, and then the obtained aqueous solution was evenly applied on the hair, heating to 40° C. with a bath cap and electric heating cap, keeping warm for 40 minutes, after that, stopping heating, the hair was washed with clear water of 20° C.;
2) 100 g of indigosol, 15 g of Carthamus tinctorious powder, 15 g of Asiatic wormwood powder, and 10 g of Fructus Gardeniae powder were mixed with 200 g of clear water of 60° C. to form a slurry with a pH value of 10, and then the obtained slurry was evenly applied on the hair, heating to 40° C. with a bath cap and electric heating cap, keeping warm for 40 minutes, after that the hair was washed by warm water;
3) 20 g of fruit acid was diluted with 300 g of clear water of 40° C. to form an aqueous solution with a pH value of 6, and then the obtained aqueous solution was evenly applied on the hair, heating to 40° C. with a bath cap and electric heating cap, keeping warm for 40 minutes, after that the hair was washed with warm water;
4) 100 g of ammonium persulfate was diluted with clear water of 20° C. to form an aqueous solution, and then the obtained aqueous solution was evenly applied on the hair, heating to 40° C. with a bath cap and electric heating cap, keeping warm for 40 minutes, after that, stopping heating, the hair was washed with clear water of 20° C. Thus, the white hair was dyed into grey brown hair.

The content of melanin of dyed black hair is equivalent to degree 3-4 of the international standard chromaticity of dyed hair; that is, dark brown or brown. The dyeing fastness of washing and sunlight can reach grade 3-4 of the international textile fiber dyeing fastness standard; that is, the dyed hair will fade slightly after washing, and will fade slightly in the sun-exposure. The glossiness of the dyed hair is <50 GU, i.e. sub-lustrous.

This comparative example shows that in the hair dyeing process according to the present application, the heating temperature has an effect on the dyeing chromaticity, dyeing fastness and glossiness; that is, in the case that other process conditions are sufficient, the lower the temperature is, the worse the dyeing chromaticity, dyeing fastness and glossiness are. On the contrary, the higher the temperature is, the better the chromaticity, dyeing fastness and glossiness are.

COMPARATIVE EXAMPLE 4

1) 5 g of potassium bicarbonate was dissolved in 200 g of clear water of 20° C. to form an aqueous solution with a pH value of 8, and then the obtained aqueous solution was evenly applied on the hair, heating to 85° C. with a bath cap and electric heating cap, keeping warm for 40 minutes, after that, stopping heating, the hair was washed with clear water of 20° C.;
2) 100 g of Polygonum tinctorium Ait. plant powder was mixed with 300 g of boiled water of 98° C. to form a slurry, and then the obtained slurry was evenly applied on the hair under the condition of pH 7, heating to 90° C. with a bath cap and electric heating cap, keeping warm for 40 minutes, after that, stopping heating, the hair was washed with clear water of 20° C.;
3) 100 g of potassium perborate was dissolved in 200 g of clear water of 20° C. to form an aqueous solution, and then the obtained aqueous solution was evenly applied on the hair, heating to 85° C. with a bath cap and electric heating cap, keeping warm for 40 minutes, after that, stopping heating, the hair was washed with clear water of 20° C.;
4) 5 g of carbonic acid was dissolved in 200 g of clear water of 20° C. to form an aqueous solution with a pH value of 6, and then the obtained aqueous solution was evenly applied on the hair, heating to 80° C. with a bath cap and electric heating cap, keeping warm for 40 minutes, after that, stopping heating, the hair was washed with clear water of 20° C. Thus, the while hair was dyed into grey brown hair.

The content of melanin of this chromaticity of dyed black hair is equivalent to degree 4-5 of the international standard chromaticity of dyed hair; that is, brown or light brown. The dyeing fastness of washing and sunlight can reach grade 2-3 of the international textile fiber dyeing fastness standard; that is, the dyed hair will somewhat fade after washing and in the sun-exposure. The glossiness of the dyed hair is <50 GU, i.e. sub-lustrous.

This comparative example shows that in the hair dyeing process according to the present application, the pH value has an effect on the dyeing chromaticity, dyeing fastness; that is, in the case of dyeing white hair into black hair, the lower the pH value of the alkaline dyeing assistant is and the higher the pH value of the acidic dyeing assistant is, the worse the chromaticity, dyeing fastness and glossiness are. On the contrary, the chromaticity, dyeing fastness and glossiness are better.

COMPARATIVE EXAMPLE 5

1) 100 g of trona was mixed with 200 g of clear water of 20° C. to form a aqueous solution with a pH value of 14, and then the obtained aqueous solution was evenly applied on the hair, heating to 90° C. with a bath cap and electric heating cap, keeping warm for 50 minutes, after that, stopping heating, the hair was washed with warm water;
2) 5 g of Polygonum tinctorium Ait. plant powder was mixed with 100 g of boiling water to form a slurry, and then the obtained slurry was evenly applied on the hair, heating to 80° C. with a bath cap and electric heating cap under the condition of pH 12, keeping warm for 50 minutes, after that, stopping heating, the hair was washed with warm water;
3) 100 g of sodium percarbonate was dissolved sufficiently in 200 g of clear water of 30° C., and then the obtained solution was evenly applied on the hair, heating to 80° C. with a bath cap and electric heating cap, keeping warm for 30 minutes, after that, stopping heating, the hair was washed warm water;
4) 30 g of sulfonic acid was dissolved sufficiently in 100 g of clear water of 20° C. to form a solution with a pH value of 4, and then the obtained solution was evenly applied on the hair, heating to 70° C. with a bath cap and electric heating cap, keeping warm for 20 minutes, after that, stopping heating, the hair was washed with warm water. Thus, the white hair was dyed into grey hair.

The chromaticity of dyed black hair reaches degree 4-5 of the international standard chromaticity of dyed hair; that is, the content of melanin is equivalent to brown or light brown. The dyeing fastness of washing and sunlight can reach grade 4-5 of the international textile fiber dyeing fastness standard; that is, the dyed hair will not fade after washing, and will not fade in the sun-exposure. The glossiness of the dyed hair is greater than 50 GU, i.e. close to high lustrous.

This comparative example shows that in the hair dyeing process according to the present application, the amount of indigo dye used has an effect on the dyeing chromaticity; that is, in the case that other process conditions are sufficient, the less the used amount of the indigo dye is, the worse the chromaticity of white hair dyed into black hair is, and the lower the blackness is. On the contrary, the blackness is higher.

COMPARATIVE EXAMPLE 6

1) 150 g of sodium carbonate was dissolved in 100 g of clear water of 20° C. to form an aqueous solution with a pH value of 14, and then the obtained aqueous solution was evenly applied on the hair, heating to 90° C. with a bath cap and electric heating cap, keeping warm for 5 minutes, after that, stopping heating, the hair was washed with clear water of 22° C.;
2) 200 g of indigo plant powder was mixed with 300 g of boiled water of 95° C. to form a slurry, and then the obtained slurry was evenly applied on the hair with a pH value of 12, heating to 90° C. with a bath cap and electric heating cap, keeping warm for 5 minutes, after that, stopping heating, the hair was washed with clear water of 22° C.;
3) 100 g of potassium permanganate was dissolved in 200 g of clear water of 20° C. to form an aqueous solution, and then the obtained aqueous solution was evenly applied on the hair, heating to 80° C. with a bath cap and electric heating cap, keeping warm for 5 minutes, after that, stopping heating, the hair was washed with clear water of 22° C.;
4) 40 g of formic acid was dissolved sufficiently in 200 g of clear water of 30° C. to form a solution with a pH value of 3, and then the obtained solution was evenly applied on the hair, heating to 80° C. with a bath cap and electric heating cap, keeping warm for 5 minutes, after that, stopping heating, the hair was washed with clear water of 20° C. Thus, the white hair was dyed into grey hair.

The chromaticity of dyed black hair reaches degree 4-5 of the international standard chromaticity of dyed hair; that is, the content of melanin is equivalent to brown or light brown.

The dyeing fastness of washing and sunlight reaches grade 2-3 of the international textile fiber dyeing fastness standard; that is, the dyed hair will somewhat fade after washing and in the sun-exposure. The glossiness of the dyed hair is <50 GU, i.e. sub-lustrous.

This comparative example shows that in the hair dyeing process according to the present application, the heating time has an effect on the dyeing chromaticity, dyeing fastness and glossiness; that is, in the case that other process conditions are sufficient, the longer the time is, the better the chromaticity, dyeing fastness and glossiness in the case of white hair dyeing into black hair are. On the contrary, the dyeing chromaticity, dyeing fastness and glossiness are worse.

COMPARATIVE EXAMPLE 7

1) 100 g of sunflower ash was mixed with 300 g of clear water of 20° C. to form a slurry with a pH value of 14, and then the obtained slurry was evenly applied on the hair, heating to 80° C. with a bath cap and electric heating cap, keeping warm for 50 minutes, after that, stopping heating, the hair was washed with warm water of 40° C.;
2) 100 g of Gardenia jasminoides Ellis plant powder and 10 g of indigo plant powder were mixed with clear water of 20° C. to form a slurry, and then the obtained slurry was evenly applied on the hair, heating to 70° C. with a bath cap and electric heating cap, keeping warm for 30 minutes, after that, stopping heating, the hair was washed with warm water of 30° C.;
3) 40 g of sodium hypochlorite was diluted with clear water of 20° C. to form an aqueous solution, and then the obtained aqueous solution was evenly applied on the hair, heating to 50° C. with a bath cap and electric heating cap, keeping warm for 30 minutes, after that, stopping heating, the hair was washed with warm water of 30° C.;
4) 20 g of sulfinic acid was diluted with clear water of 20° C. to form an aqueous solution, and then the obtained aqueous solution was evenly applied on the hair, heating to 50° C. with a bath cap and electric heating cap, keeping warm for 30 minutes, after that, stopping heating, the hair was washed with clear water of 20° C. Thus, the white hair was dyed into brown hair.

The chromaticity of dyed hair can reach degree 4 of the international standard chromaticity of dyed hair; that is, brown. The dyeing fastness reaches grade 4-5 of the international textile fiber dyeing fastness standard; that is, the dyed hair will not fade after washing, and will not fade in the sun-exposure. The glossiness of the dyed hair is greater than 70 GU, i.e. close to high lustrous.

This comparative example shows that in the hair dyeing process according to the present application, in the case of dyeing hair with other plant dyes, the use of small amount of plant indigo dye can increase the depth or blackness of the color dyed and get a relatively strong color; that is, the more the used amount of the indigo is, the higher the depth or blackness is. On the contrary, the depth or blackness is lower.

The description of the above examples is only used to help understand the method according to the present application and its core idea. It should be noted that for those ordinarily skilled in the art, several improvements and modifications can be made to the present application without departing from the principles of the application, which also fall within the protection scope of the claims of the application.

The above description of the disclosed examples enables those skilled in the art to realize or use the present application. Various modifications to these examples will be apparent to those skilled in the art, and the general principles defined herein can be implemented in other examples without departing from the spirit or scope of the application. Therefore, the present application will not be limited to these examples shown herein, but will conform to the widest scope consistent with the principles and novel features disclosed herein.

What is claimed is:

1. An indigo darkener, comprising:
   an indigo dye: 20-40 parts by weight;
   an alkaline dyeing assistant: 5-10 parts by weight;
   an acidic dyeing assistant: 4-20 parts by weight;
   an oxidizing agent: 2-10 parts by weight; and
   a dyeing supplement: 0.5-20 parts by weight.

2. The indigo darkener according to claim 1, wherein the indigo dye is selected from one or more of a natural plant indigo dye and a synthetic indigo dye, wherein the natural plant indigo dye is made by fermentation of plant leaves containing indolic acid component, and the natural plant indigo dye is selected from one or more of plant indigo and plant indigo naturalis; the synthetic indigo dye is selected from one or more of food blue 1, food blue 2, brilliant blue, acidic indigo, hardened indigo, C.1. pigment blue 66, monolite navy blue BV, C.1. reduced blue 1,2,2-diazaindene indigo, indigo, pure indigo, indigo (1), XianShaJianDing synthetic indigo/2, indigo powder, reduced indigo, indigosol and indigoidine; the indigo dye is other plant dyes that are easy to be oxidized to form carbon black or black carbon oxide;
   the alkaline dyeing assistant is selected form one or more of organic alkali, inorganic alkali and other alkali substances with alkaline pH value;
   the acidic dyeing assistant is selected from one or more of organic acid, inorganic acid and other acidic substances with acidic pH value; and
   the oxidizing agent is selected from one or more of organic oxidizing agent, inorganic oxidizing agent, neutral oxidizing agent and other oxidizing substances with oxidation effect.

3. The indigo darkener according to claim 1, wherein the dyeing supplement is selected from one or more of camphire, madder, henna, Impatiens balsamina, mignonettetree, lawsonia inermis L, leaf of henna, Impatiens balsamina L, amaranth, Syzygium aromaticum, Morus nigra, mulberry, sorosis, hispid arthraxon, Perillae Fructus, common bletilla tuber, indigotin, Algal lotus, radix lithospermi, sapanwood, hematoxylin, indigo, Carthamus tinctorious, punicagranatum, Gardenia jasminoides Ellis, Fructus Gardeniae, Artemisia argyi, rheum officinale, the fruit of Chinese magnoliavine, isatis root, blue grass, jiangjin, Flos Sophorae Immaturus, Rhamnus utilis, shell of an acorn, chinese sapium, Chinese gall, acorn shell, chestnut rind, lotus seed shell, persimmon, alums, avocado fruit, Polygonum multiflorum, sappan lignum, dye yam, Excoecaria sebifera, Buchnera cruciatas Hamilt, Asiatic wormwood, Strobilanthes cusia, Polygonum tinctorium Ait., Isatis indigotica Fortune, purple perilla, Haematoxylum campechianum, red wine, coffee, tea, indigo naturalis, carbon black, conductex, beer, lemon and Chrysanthemum morifolium Ramat extract.

4. A hair dyeing process using an indigo darkener, comprising following steps:
   A) mixing 0-99 parts by weight of an alkaline dyeing assistant with water, applying an obtained mixture on hair, heating and keeping warm, and then rinsing the hair with water, with a content of the alkaline dyeing assistant being not 0; or heating the hair at high temperature, with a content of the alkaline dyeing assistant being 0;
- B) mixing 0.1-99 parts by weight of an indigo dye with water, applying an obtained mixture on the hair obtained in the step A), heating and keeping warm, and then rinsing the hair with water;
- C) mixing 0-99 parts by weight of an oxidizing agent with water, applying an obtained mixture on the hair obtained in the step B), heating and keeping warm, and then rinsing the hair with water, with a content of the oxidizing agent being not 0; or
oxidizing the hair obtained in the step B) naturally, with a content of the oxidizing agent being 0; and
- D) mixing 0.01-99 parts by weight of an acidic dyeing assistant with water, applying an obtained mixture on the hair obtained in the step C), heating and keeping warm, and then rinsing the hair with water.

5. The hair dyeing process according to claim 4, wherein in the step A) and/or the step B), the mixture further comprises 0.001-99 parts by weight of a dyeing supplement.

6. The hair dyeing process according to claim 4, wherein the hair dyeing process further comprises, after the step B):
- B') mixing 0.001-99 parts by weight of a dyeing supplement with water, applying an obtained mixture on the hair obtained in the step B), heating and keeping warm, and then rinsing the hair with water.

7. The hair dyeing process according to claim 6, wherein when the content of the oxidizing agent is not 0, the hair dyeing process further comprises, after the step B) and before the step B'):
- B") naturally oxidizing the hair obtained in the step B), wherein the natural oxidation is in a manner of oxidation in air, blowing hot air or sun exposure.

* * * * *